United States Patent [19]

Davies et al.

[11] 4,103,017
[45] Jul. 25, 1978

[54] PESTICIDAL 2-IMINOTHIAZOLINE DERIVATIVES

[75] Inventors: John H. Davies, Boughton; Jack Wood; Michael Pearson, both of Sittingbourne, all of England

[73] Assignee: Shell Oil Company, Houston, Tex.

[21] Appl. No.: 775,500

[22] Filed: Mar. 8, 1977

[30] Foreign Application Priority Data

Mar. 9, 1976 [GB] United Kingdom ............... 9335/76

[51] Int. Cl.² ................ C07D 277/18; A61K 31/425
[52] U.S. Cl. ............................ 424/270; 260/306.7 T
[58] Field of Search ................ 260/306.7 T; 424/270

[56] References Cited

FOREIGN PATENT DOCUMENTS 7,417,059  7/1975  Netherlands ............... 260/306.7

*Primary Examiner*—Nicholas S. Rizzo

[57] ABSTRACT

2-Iminothiazoline derivatives of the formula:

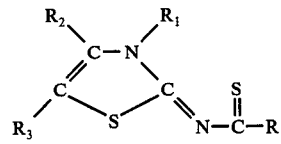

and the corresponding 4,5-dihydro counterparts, wherein the respective meanings of the symbols are set forth in the specification, useful as insecticides and acaricides.

3 Claims, No Drawings

PESTICIDAL 2-IMINOTHIAZOLINE DERIVATIVES

DESCRIPTION OF THE INVENTION

The present invention relates to novel thiazoline derivatives to be specified hereinafter as well as to processes for their preparation. The thiazoline derivatives according to the present invention have interesting insecticidal and acaricidal properties. The present invention therefore also relates to compositions comprising a carrier or a surface active agent or both a carrier and a surface active agent and at least one of the thiazoline derivatives to be specified hereinafter. The present invention relates also to a method of combating insects and/or acarids by applying to a locus a thiazoline derivative according to the present invention or a composition comprising at least one thiazoline derivative according to the present invention.

The novel compounds according to the present invention are 2-imino-thiazoline derivatives of the general formula:

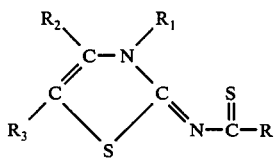

wherein R and $R_1$ each individually represents hydrogen, an optionally substituted alkyl, alkenyl, alkynyl, alkoxy, alkoxycarbonyl, aryl or alkaryl group and $R_2$ and $R_3$ each individually represents hydrogen, halogen, an optionally substituted alkyl, alkenyl, thioalkyl, alkoxy, aryl or alkaryl group or $R_2$ and $R_3$ together with the vinylene group to which they are attached from an optionally substituted carbocyclic or heterocyclic ring and the corresponding 4,5-dihydro compounds.

Preferred 2-imino-thiazolines are those of formula I wherein R represents hydrogen, an alkyl group of from 1 to 6 carbon atoms, or an aryl group; $R_1$ represents an alkyl or alkenyl group of up to 12 carbon atoms or an alkaryl group; $R_2$ and $R_3$ each represents hydrogen, chlorine or bromine, an alkyl or thioalkyl group of from 1 to 6 carbon atoms or an aryl group or $R_2$ and $R_3$ together with the vinylene group to which they are attached form an optionally substituted six-membered ring.

Particularly preferred 2-imino-thiazoline derivatives are those of formula I wherein R represents a methyl, isopropyl or phenyl group; $R_1$ represents a methyl, ethyl, isopropyl, n-decyl or allyl group and $R_2$ and $R_3$ each individually represents a hydrogen atom.

The 2-imino-thiazoline derivatives according to the present invention may be prepared by a process which comprises reacting a compound of formula:

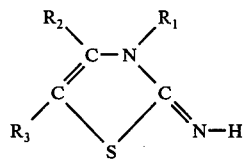

with a compound of formula:

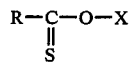

wherein R, $R_1$, $R_2$ and $R_3$ are as defined hereinabove and X represents a lower alkyl group of 1 to 6 carbon atoms, suitably an ethyl group. The reaction is suitably carried out in a solvent such as dioxane or ethanol at slightly elevated temperatures, e.g. at reflux conditions.

The 2-imino-thiazoline derivatives according to the present invention may also be suitably prepared by reacting a compound of formula:

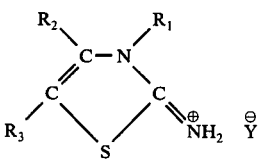

with a compound of formula:

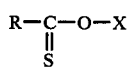

wherein R, $R_1$, $R_2$, $R_3$ and X are as defined hereinabove and Y represents a bromide, iodide or (hydro) sulphate ion and espectially an iodide ion, in the presence of a base. Alkalihydroxides, such as sodium hydroxide, are suitable bases. Preferably the reaction is carried out in the presence of a solvent such as ethanol or acetone. The reactions may be carried out at ambient temperature or at slightly elevated temperatures, e.g. at the boiling point of the solvent employed. Good yields are obtained by adding an aqueous solution of sodium hydroxide at room temperature to an ethanolic solution of the 2-imino-thiazolinium iodide concerned followed by addition of the appropriate thiocarboxylic acid ester.

As mentioned above the 2-imino-thiazoline derivatives according to the invention are of interest as pesticides and the invention therefore includes pesticidal compositions comprising a carrier and/or a surface-active agent together with a 2-imino-thiazoline derivative of formula I. Likewise the invention also includes a method of combating insect or acarid pests at a locus which comprises applying to the locus a 2-imino-thiazoline derivative or composition according to the invention.

The 2-imino-thiazoline derivatives according to the present invention are especially active against vetch aphids (*Megoura viciae*) and spider mites (*Tetranychus urticae*).

They also exhibit useful activity against insect pests of rice such as stem borers and in particular against the leaf hoppers. The stem borers belong mainly to two families of Lepidoptera, the Pyralids, which include the various species of Chilo, and the Noctuids which include *Sesamia inferens*. The larvae of these insects penetrate into the stem of the rice plant shortly after hatching on the leaf, and feed on the inner surface of the stem walls, either killing the plant or injuring it so much that it produces no grains. The leaf hoppers are Hemiptera and are members either of the family Delphacidae, for example Nilaparvata, or of the family Cicadellidae, for example Nephotettix. These insects can effect growing rice plants in the following ways; by sucking sap from the leaves, by damaging the conductive tissue of the plants and by acting as transmitters of various virus diseases of rice plants.

The term 'carrier' as used herein means a solid or fluid material, which may be inorganic or organic and of synthetic or natural origin, with which the active compound is mixed or formulated to facilitate its application to the plant, seed, soil or other object to be treated, or its storage, transport or handling.

The surface-active agent may be an emulsifying agent or a dispersing agent or a wetting agent; it may be non-ionic or ionic.

Any of the carrier materials or surface-active agents usually applied in formulating pesticides may be used in the compositions of the invention, and suitable examples of these are to be found, for example, in British Patent Specification No. 1,232,930.

The compositions of the invention may be formulated as wettable powders, dusts, granules, solutions, emulsifiable concentrates, emulsions, suspension concentrates or aerosols. Wettable powders are usually compounded to contain 25, 50 or 75% of toxicant and usually contain, in addition to solid carrier, 3–10% w of a dispersing agent and, where necessary, 0–10% w of stabilizer(s) and/or additives, such as penetrants or stickers.

Dusts are usually formulated as a dust concentrate having a similar composition to that of a wettable powder but without a dispersant, and are diluted in the field with further solid carrier to give a composition usually containing 0.5–10% w of toxicant. Granules are usually prepared to have a size between 10 and 100 BS mesh (1.676–0.152 mm), and may be manufactureed by agglomeration or impregnation techniques. Generally, granules will contain 0.5–25% w toxicant and 0–10% w of additives such as stabilizers, slow release modifiers and binding agents. Emulsifiable concentrates usually contain, in addition to the solvent and, when necessary, co-solvent, 10–50% w/v toxicant, 2–20% w/v emulsifiers and 0–20% w/v of appropriate additives such as stabilizers, penetrants and corrosion inhibitors. Suspension concentrates are compounded so as to obtain a stable, non-sedimenting, flowable product and usually contain 10–75% w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing pesticidal, especially insecticidal, acaricidal, herbicidal or fungicidal properties.

The invention is further illustrated in the following Examples:

EXAMPLE 1 — preparation of 2-thioacetimido-3-methyl thiazoline

A solution of 13.2 g (0.33 m) sodium hydroxide in 50 ml water was added dropwise at room temperature to a stirred solution of 2-imino-3-methyl thiazolinium iodide (80 g, 0.33 m) in 500 ml ethanol. Ethylthiono acetate (35 g, 0.36 m) was added at ambient temperature to the stirred mixture. The mixture obtained was heated under reflux conditions for five hours. After cooling, the solution was poured onto 500 ml water. The aqueous solution was twice extracted with 500 ml portions of dichloromethane. The organic layer was separated and dried over magnesium sulphate. Dichloromethane was removed under vacuum. The yellow solid obtained was purified by recrystallization from toluene to give 40 g (yield 70%) 2-thioacetimido-3-methyl thiazoline, m.p. 139°–141° C.

Analysis: $C_6H_8N_2S_2$ Calculated: C 41.83; H 4.68; N 16.27% Found: C 41.6; H 4.7; N 16.1%

EXAMPLE 2 — preparation of 2-thioheptoylimido-3-methyl thiazoline 2-imino-3-methyl thiazolinium iodide (15 g. 0.062 m) was dissolved in ethanol (100 ml). Sodium hydroxide (2.48 g. 0.062 m) in water (10 ml) was added dropwise to the stirred solution at ambient temperature, followed by the addition of ethylthiono octanoate (11.65 g 0.062 m). The mixture was heated under reflux conditions for 16 hours The cooled solution was poured onto water (100 ml) and extracted twice with 100 ml portions of dichloromethane. The organic layer was separated and dried ($MgSO_4$). After removal of the solvent, a red oil was obtained which was purified by column chromatography (silica (300 g) using dichloromethane as eluent). The product was recrystallized from cyclohexane. Yield 10.25 g (71%) m.p. 52°–53° C.

Analysis: $C_{12}H_{20}N_2S_2$ Calculated: C 56.20; H 7.86; N 10.93% Found: C 56.6; H 7.8; N 10.6%

EXAMPLE 3 — preparation of 2-thioacetimido-3-methyl-4-sec. butyl thiazoline (1) and 2-thioacetimido-3,4-dimethyl-5-isopropyl thiazoline (2)

A mixture of 2-imino-3-methyl-4-sec. butyl thiazolinium iodide and 2-imino-3,4-dimethyl-5-isopropyl thiazolinium iodide (33.5 g, 0.112 m, obtained by reacting a mixture of the corresponding amino compounds with methyliodide in ethanol) was dissolved in ethanol (250 ml). Sodium hydroxide (4.5 g, 0.112 m) in water (25 ml) was added dropwise to the stirred solution at ambient temperature, followed by the addition of ethylthiono acetate (11.7 g, 0.112 m). The mixture was heated under reflux conditions for 16 hours. The cooled solution was poured onto water (250 ml) and extracted twice with 250 ml portions of dichloromethane. The organic layer was separated and dried ($MgSO_4$). Dichloromethane was removed under vacuum. The mixture of products obtained was separated using column chromatography on silica gel (300 g) with toluene as eluent. The separated products were recrystallized from cyclohexane. Total yield 15.6 g (64%). m.p. (1) 128°–129° C, m.p. (2) 149°–150° C.

Analysis: $C_{10}H_{16}N_2S_2$ (1) (2) Calculated: C 52.59; H 7.06; N 12.27% (1) Found: C 52.3; H 7.1; N 12.2% (2) Found: C 52.5; H 7.1; N 11.9%

EXAMPLE 4 — preparation of 2-thioacetimido-3-allyl thiazoline

To 2-imino-3-allyl-thiazoline (8 g, 0.057 m) in dry dioxane was added ethylthiono acetate (5.94 g, 0.057 m). The mixture was stirred under reflux conditions for 5 hours. The solution was cooled and the solvent removed under vacuum. The product obtained was purified by column chromatography using silica and dichloromethane as eluent. The yield was 4.1 g (36%) m.p. 76°–78° C.

Analysis: $C_8H_{10}N_2S_2$ Calculated: C 48.45; H 5.08; N 14.13% Found: C 48.0; H 4.9; N 14.0%

EXAMPLES 5–42

Following procedures similar to those described in the foregoing Examples, further compounds according to the invention were prepared whose physical characteristics and analytical data are set out in Table I below.

EXAMPLE 43 — insecticidal and acaricidal activity

The insecticidal and acaricidal activity of the compounds according to the invention was tested as follows: I. The compounds were formulated as solutions or suspensions in water containing 20% by weight of acetone and 0.05% by weight of Triton X 100 as wetting agent. The formulations contained 0.7% by weight of the compound to be tested. Broad bean plants, trimmed to one leaf each, were sprayed on the undersurface of the leaf with the above formulation. Spraying was effected with a spraying machine delivering 450 liters per hectare, the plants passing under the spray on a moving belt. Ten apterous (6-day-old) vetch aphids (*Megoura viciae*) were placed on the sprayed leaf of each broad bean plant. The plants were then enclosed in glass cylinders fitted at one end with a muslin cap. Mortality counts were made after 24 hours. II. In tests against glass house spider mites (*Tetranychus urticae*), leaf discs cut from French bean plants were sprayed in the manner described under I, 1 hour after spraying, the discs were inoculated with 10 adult mites. Mortality counts were made 24 hours after inoculation. III. Activity against insect pests of rice.

A. Activity against stemborers

Rice plants (Oryza sativa) were grown to a height of 30 cm in paddy soil contained in small pots. The number of tillers in each pot was reduced to 4 and each tiller was infested with 5 newly hatched larvae of the striped rice borer (*Chilo suppressalis*) (Cs). The infested plants were maintained at 25° C in a glasshouse for 5 days. The plants were then strayed with solutions of the test compound in a 9:1 mixture of water and acetone containing 0.5% Triton-X-100 as wetting agent. The sprayed plants were dissected 5 days after spraying and the number of dead larvea was assessed.

B. Activity against leaf hoppers

Single rice plants (height 15 cm) in small pots were sprayed with solutions of the test compound as described under A. One hour after spraying the plants were infested with 20 five-day old adult female hoppers of one or other of the following species:

*Nephotettix cincticeps* (Nc)
*Nilaparvata lugens* (Nl)
*Laodelphax striatella* (Ls)

In the case of the latter two species only long winged adults were used. Mortalities were assessed after 24 hours.

The results of the tests against vetch aphids (M.v.) and spider mites (T.u.) are shown in Table II in which 2 denotes greater than 80% kill, 1 50–80% kill and 0 less than 50% kill of the test species. The results of the tests against the insect pests of rice are given in Table III. The doses applied are equal to 0.5 kg/ha.

TABLE I

| Ex. No. | R | $R_1$ | $R_2$ | $R_3$ | m.p. | |
|---|---|---|---|---|---|---|
| 5 | i-$C_3H_7$ | $CH_3$ | H | H | 44–45° C | Calc. for $C_8H_{12}N_2S_2$: C 47.97; H 6.04; N 13.99% <br> Found : C 48.2; H 6.2; N 14.1% |
| 6 | phenyl | $CH_3$ | H | H | 126–127° C | Calc. for $C_{11}H_{10}N_2S_2$: C 56.4; H 5.1; N 11.9% <br> Found : C 56.7; H 5.2; N 11.8% |
| 7 | $CH_3$ | benzyl | H | H | 102–103° C | Calc. for $C_{12}H_{12}N_2S_2$: C 58.03; H 4.8; N 11.3% <br> Found : C 58.2; H 5.0; N 11.4% |
| 8 | $CH_3$ | $C_2H_5$ | H | H | 83–58° C | Calc. for $C_7H_{10}N_2S_2$: C 45.13; H 5.4; N 15.0% <br> Found : C 45.5; H 5.4; N 14.8% |
| 9 | i-$C_3H_7$ | $C_2H_5$ | H | H | $n_D^{18}$ = 1.6485 | Calc. for $C_9H_{14}N_2S_2$: C 50.4; H 6.6; N 13.07% <br> Found : C 50.5; H 6.6; N 13.1% |
| 10 | phenyl | $C_2H_5$ | H | H | 140–141° C | Calc. for $C_{12}H_{12}N_2S_2$: C 58.03; H 4.87; N 11.3% <br> Found : C 58.1; H 4.8; N 11.3% |
| 11 | $CH_3$ | $CH_3$ | $CH_3$ | $CH_3$ | 150° C | Calc. for $C_8H_{12}N_2S_2$: C 48.0; H 6.0; N 14.0% <br> Found : C 48.0; H 6.1; N 14.0% |
| 12 | $CH_3$ | $CH_2CO_2C_2H_5$ | H | H | 100° C | Calc. for $C_9H_{12}O_2N_2S_2$: C 44.2; H 4.9, N 11.5% <br> Found : C 44.5; H 4.9; N 11.4% |
| 13 | H | $CH_3$ | H | H | 113° C | Calc. for $C_5H_6N_2S_2$: C 38.2; H 3.8; N 17.8% <br> Found : C 37.9; H 3.8; N 17.8% |
| 14 | $CH_3$ | n-$C_3H_7$ | H | H | 54–56° C | Calc. for $C_8H_{12}N_2S_2$: C 47.96; H 6.04; N 13.98% <br> Found : C 47.4; H 6.3; N 13.7% |
| 15 | $CH_3$ | i-$C_3H_7$ | H | H | oil | Calc. for $C_8H_{12}N_2S_2$: C 47.96; H 6.04; N 13.98% <br> Found : C 48.3; H 6.2; N 13.9% |
| 16 | $CH_3$ | n-$C_{10}H_{21}$ | H | H | 43–44° C | Calc. for $C_{15}H_{26}N_2S_2$: C 60.35; H 8.87; N 9.39% <br> Found : C 60.2; H 8.7; N 9.0% |
| 17 | phenyl | $CH_3$ | H | H Saturated | 119–120° C | Calc. for $C_{11}H_{12}N_2S_2$: C 55.9; H 5.1; N 11.9% S 27.1% <br> Found : C 55.5; H 5.0; N 12.1; S 27.2% |
| 18 | $CH_3$ | $CH_3$ | H | H Saturated | 87–89° C | Calc. for $C_6H_{10}N_2S_2$: C 41.4; H 5.8; N 16.1% <br> Found : C 41.9; H 5.6; N 15.2% |
| 19 | $CH_3$ | $CH_3$ | | 6-MeO-phenyl | 138° C | Calc. for $C_{11}H_{12}ON_2S_2$: C 52.5; H 4.79; N 11.1% <br> Found : C 52.2; H 4.6; N 11.0% |
| 20 | $CH_3$ | $CH_3$ | | 4-MeO-phenyl | 173° C | Calc. for $C_{11}H_{12}ON_2S_2$: C 52.35; H 4.79; N 11.1% <br> Found : C 52.2; H 4.6; N 11.0% |
| 21 | $CH_3$ | $CH_3$ | | phenyl | 140° C | Calc. for $C_{10}H_{10}N_2S_2$: C 54.02; H 4.53; N 12.6% <br> Found : C 53.9; H 4.4; N 12.4% |
| 22 | $CH_3$ | $CH_3$ | $CH_3$ | Br | | Calc. for $C_7H_9N_2S_2Br$: C 31.7; H 3.42; N 10.56% <br> Found : C 32.0; H 3.3; N 10.4% |
| 23 | $CH_3$ | $CH_3$ | $C_2H_5$ | H | 117° C | Calc. for $C_8H_{12}N_2S_2$: C 48.0; H 6.04; N 13.99% |

TABLE I-continued

| Ex. No. | R | $R_1$ | $R_2$ | $R_3$ | m.p. | Analysis |
|---|---|---|---|---|---|---|
| 24 | phenyl | $CH_3$ | $C_2H_5$ | H | 180–181° C | Calc. for $C_{13}H_{14}N_2S_2$: C 59.50; H 5.38; N 10.68% <br> Found: C 59.4; H 5.4; N 10.5% |
| 25 | phenyl | $CH_3$ | $CH_3$ | $CH_3$ | 235° C | Calc. for $C_{13}H_{14}N_2S_2$: C 59.50; H 5.38; N 10.68% <br> Found: C 59.9; H 5.5; N 10.5% |
| 26 | n-$C_3H_7$ | $CH_3$ | H | H | 97–98° C | Calc. for $C_8H_{12}N_2S_2$: C 47.96; H 6.0; N 13.99% <br> Found: C 47.9; H 6.0; N 13.9% |
| 27 | $CH_3$ | $CH_3$ | phenyl | H | 133–134° C | Calc. for $C_{12}H_{12}N_2S_2$: C 58.03; H 4.87; N 11.28% <br> Found: C 57.9; H 4.8; N 11.1% |
| 28 | $CH_3$ | $CH_3$ | t-butyl | H | 82–85° C | Calc. for $C_{10}H_{16}N_2S_2$: C 52.59; H 7.06; N 12.27% <br> Found: C 52.2; H 7.1; N 12.0% |
| 29 | $CH_3$ | $CH_3$ | i-$C_3H_7$ | H | 160–162° C | Calc. for $C_9H_{14}N_2S_2$: C 50.43; H 6.58; N 13.07% <br> Found: C 50.5; H 6.8; N 12.9% |
| 30 | $CH_3$ | $CH_3$ | n-$C_3H_7$ | H | 109–110° C | Calc. for $C_9H_{14}N_2S_2$: C 50.43; H 6.58; N 13.07% <br> Found: C 50.6; H 6.6; N 13.0% |
| 31 | $CH_3$ | $CH_3$ | $C_2H_5$ | $CH_3$ | 125–126° C | Calc. for $C_9H_{14}N_2S_2$: C 50.43; H 6.58; N 13.07% <br> Found: C 50.3; H 6.5; N 12.7% |
| 32 | —$(CH_2)_{11}CH_3$ | $CH_3$ | H | H | 67–68° C | Calc. for $C_{14}H_{30}N_2S_2$: C 62.52; H 9.26; N 8.58% <br> Found: C 62.1; H 9.3; N 8.3% |
| 33 | $CH_3$ | —$CH_2$—C≡CH | H | H | 114–116° C | Calc. for $C_8H_8N_2S_2$: C 48.95; H 4.11; N 14.27% <br> Found: C 48.8; H 4.0; N 14.2% |
| 34 | i-$C_3H_7$ | $(CH_2)_9CH_3$ | H | H | 30–31° C | Calc. for $C_{17}H_{30}N_2S_2$: C 62.52; H 9.26; N 8.5% <br> Found: C 62.6; H 9.2; N 8.5% |
| 35 | n-$C_3H_7$ | $(CH_2)_2CH_3$ | H | H | Oil | Calc. for $C_{10}H_{16}N_2S_2$: C 52.59; H 7.06; N 12.27% <br> Found: C 52.5; H 7.2; N 11.6% |
| 36 | n-$C_3H_7$ | $C_2H_5$ | H | H | 50–52° C | Calc. for $C_9H_{14}N_2S_2$: C 50.43; H 6.58; N 13.07% <br> Found: C 50.5; H 6.9; N 12.8% |
| 37 | $(CH_2)_4CH_3$ | $CH_3$ | H | H | 57–58° C | Calc. for $C_{10}H_{16}N_2S_2$: C 52.59; H 6.06; N 12.27% <br> Found: C 52.8; H 7.3; N 12.1% |
| 38 | $(CH_2)_4CH_3$ | $(CH_2)_2CH_3$ | H | H | Oil | Calc. for $C_{12}H_{20}N_2S_2$: C 56.20; H 7.86; N 10.93% <br> Found: C 56.7; H 8.0; N 10.3% |
| 39 | $C_2H_5$ | $CH_3$ | H | H | 74–76° C | Calc. for $C_7H_{10}N_2S_2$: C 45.13; H 5.41; N 15.04% <br> Found: C 45.5; H 5.1; N 15.2% |
| 40 | $C_2H_5$ | $C_2H_5$ | H | H | 65–66° C | Calc. for $C_8H_{12}N_2S_2$: C 47.96; H 6.04; N 13.99% <br> Found: C 48.1; H 6.2; N 14.0% |
| 41 | $CH_3$ | $\overset{Cl}{\underset{}{\mid}}$ <br> $CH_2C{=}CH_2$ | H | H | 78–81° C | Calc. for $C_8H_9N_2S_2Cl$: C 41.28; H 3.9; N 12.04% <br> Found: C 41.4; H 4.0; N 11.6% |
| 42 | $CH_3$ | $CH_2CH{=}\underset{CH_3}{\overset{Cl}{C}}$ | H | H | 64–65° C | Calc. for $C_9H_{11}N_2S_2Cl$: C 43.4; H 4.6; N 11.2% <br> Found: C 43.4; H 4.6; N 11.2% |

TABLE II

| Compound | | Activity | | | |
|---|---|---|---|---|---|
| R | $R_1$ | $R_2$ | $R_3$ | M.v. | T.u. |
| $CH_3$ | $CH_3$ | H | H | 2 | 2 |
| i-$C_3H_7$ | $CH_3$ | H | H | 2 | 2 |
| phenyl | $CH_3$ | H | H | 2 | 2 |
| $CH_3$ | $C_2H_5$ | H | H | 2 | 2 |
| i-$C_3H_7$ | $C_2H_5$ | H | H | 2 | 2 |
| phenyl | $C_2H_5$ | H | H | 2 | 2 |
| $CH_3$ | i-$C_3H_7$ | H | H | 0 | 2 |
| $CH_3$ | n-$C_{10}H_{21}$ | H | H | 2 | 1 |

TABLE III

| | Activity | | | |
|---|---|---|---|---|
| Example | Cs | Nc | Nl | Ls |
| 1 | 15.5 | 91.5 | 61.7 | 96.6 |
| 5 | 4.8 | 80.0 | 3.3 | 8.5 |
| 6 | 10.9 | 26.7 | 0 | 3.3 |
| 8 | 10.6 | 91.7 | — | 0 |
| 9 | 8.1 | 84.7 | — | 0 |

—: not determined

We claim:

1. A 2-iminothiazoline derivative of the formula:

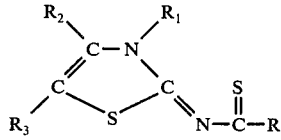

wherein R is hydrogen, alkyl of one to six carbon atoms, or phenyl; $R_1$ is alkyl or alkenyl of up to twelve carbon atoms, or is benzyl; $R_2$ and $R_3$ each is hydrogen, chlorine, bromine, alkyl or alkylthio of one to six carbon atoms, or is phenyl.

2. A method for killing insects and acarids which comprises subjecting them to an effective amount of a compound of claim 1.

3. A composition adapted to killing insects and acarids which comprises an effective amount of a compound of claim 1 together with a carrier, optionally containing in addition thereto a surface-active agent.